(12) United States Patent
Kaiser et al.

(10) Patent No.: US 8,162,967 B1
(45) Date of Patent: Apr. 24, 2012

(54) METHOD AND APPARATUS FOR CORING AND REAMING OF BONE

(75) Inventors: Ryan A Kaiser, Leesburg, IN (US); Kevin T Stone, Winona Lake, IN (US)

(73) Assignee: Biomet Sports Medicine LLC, Warsaw, IN (US)

( * ) Notice: Subject to any disclaimer, the term of this patent is extended or adjusted under 35 U.S.C. 154(b) by 2085 days.

(21) Appl. No.: 10/687,108

(22) Filed: Oct. 16, 2003

(51) Int. Cl.
*A61B 17/14* (2006.01)

(52) U.S. Cl. ............... 606/180; 279/82; 279/97

(58) Field of Classification Search .......... 606/180; 279/74, 82, 50, 97
See application file for complete search history.

(56) References Cited

U.S. PATENT DOCUMENTS

| | | | |
|---|---|---|---|
| 493,730 | A | 3/1893 | MacKenzie |
| 1,848,590 | A | 3/1932 | Willis |
| 1,911,873 | A | 5/1933 | Balton |
| 2,062,257 | A | 12/1934 | Douglas et al. |
| 2,573,462 | A | 10/1951 | Lindsey |
| 2,591,516 | A | 4/1952 | Darnell |
| 2,754,864 | A | 7/1956 | Elsy |
| 2,779,361 | A | 1/1957 | McKiff |
| 3,430,526 | A | 3/1969 | Valenziano |
| 3,609,056 | A | 9/1971 | Hougen |
| 3,848,601 | A | 11/1974 | Ma et al. |
| 4,007,732 | A | 2/1977 | Kvavle et al. |
| 4,010,737 | A | 3/1977 | Vilaghy et al. |
| 4,059,115 | A | 11/1977 | Jumashev et al. |
| 4,177,797 | A | 12/1979 | Baylis et al. |
| 4,596,243 | A | 6/1986 | Bray |
| 4,649,918 | A | 3/1987 | Pegg et al. |
| 4,741,651 | A | 5/1988 | Despres |
| 4,772,286 | A | 9/1988 | Goble et al. |
| 4,779,689 | A | 10/1988 | Paxton, III |
| 4,782,833 | A | 11/1988 | Einhorn et al. |
| 4,830,000 | A | 5/1989 | Shutt |
| 4,856,693 | A * | 8/1989 | Kageyama et al. ........... 226/127 |
| 4,862,882 | A | 9/1989 | Venturi et al. |
| 4,865,146 | A | 9/1989 | Ohe |
| 4,895,146 | A | 1/1990 | Draenert |
| 4,901,711 | A | 2/1990 | Goble et al. |
| 4,913,143 | A * | 4/1990 | Oloff et al. .................... 606/170 |
| 4,927,421 | A | 5/1990 | Goble et al. |
| 4,936,313 | A | 6/1990 | Burkhardt et al. |
| 4,950,270 | A | 8/1990 | Bowman et al. |
| 4,985,032 | A | 1/1991 | Goble |

(Continued)

FOREIGN PATENT DOCUMENTS

DE 19503504 3/1996

(Continued)

OTHER PUBLICATIONS

Anthrotek, Inc., Autogeneous Bone Coring: A Scientific Approach, 2004.*

(Continued)

*Primary Examiner* — S. Thomas Hughes
*Assistant Examiner* — Julie A Szpira
(74) *Attorney, Agent, or Firm* — Harness, Dickey (57) ABSTRACT

A method and apparatus for providing an implant of autogenous bone. Generally, the implant may be taken from a selected bone portion and implanted into another selected bone portion within during a procedure. The method may be used in conjunction with soft tissue reinsertion or attachment to the selected implant site.

20 Claims, 11 Drawing Sheets

U.S. PATENT DOCUMENTS

| | | | |
|---|---|---|---|
| 4,997,434 A * | 3/1991 | Seedhom et al. | 606/80 |
| 5,037,426 A | 8/1991 | Goble et al. | |
| 5,082,403 A | 1/1992 | Sutton | |
| 5,129,902 A | 7/1992 | Goble et al. | |
| 5,139,499 A | 8/1992 | Small et al. | |
| 5,139,520 A | 8/1992 | Rosenberg | |
| 5,147,362 A | 9/1992 | Goble | |
| 5,152,763 A | 10/1992 | Johnson | |
| 5,190,548 A | 3/1993 | Davis | |
| 5,197,967 A | 3/1993 | Wilson | |
| 5,205,685 A | 4/1993 | Herbert | |
| 5,211,647 A | 5/1993 | Schmieding | |
| 5,257,996 A | 11/1993 | McGuire | |
| 5,269,786 A | 12/1993 | Morgan | |
| 5,320,115 A | 6/1994 | Kenne | |
| 5,320,626 A | 6/1994 | Schmieding | |
| 5,341,816 A | 8/1994 | Allen | |
| 5,391,170 A | 2/1995 | McGuire et al. | |
| 5,397,357 A | 3/1995 | Schmieding et al. | |
| 5,415,651 A | 5/1995 | Schmieding | |
| 5,423,823 A | 6/1995 | Schmieding | |
| 5,496,326 A | 3/1996 | Johnson | |
| 5,520,693 A | 5/1996 | McGuire et al. | |
| 5,562,669 A | 10/1996 | McGuire | |
| 5,591,170 A | 1/1997 | Spievack et al. | |
| 5,603,716 A | 2/1997 | Morgan et al. | |
| 5,632,747 A * | 5/1997 | Scarborough et al. | 606/79 |
| 5,697,935 A | 12/1997 | Moran et al. | |
| 5,772,664 A * | 6/1998 | DeSatnick et al. | 606/80 |
| 5,782,835 A | 7/1998 | Hart et al. | |
| 5,785,714 A | 7/1998 | Morgan et al. | |
| 5,803,678 A | 9/1998 | Korb et al. | |
| 5,865,834 A | 2/1999 | McGuire | |
| 5,918,604 A | 7/1999 | Whelan | |
| 5,919,196 A * | 7/1999 | Bobic et al. | 606/86 R |
| 5,928,238 A | 7/1999 | Scarborough et al. | |
| 6,017,348 A * | 1/2000 | Hart et al. | 606/79 |
| 6,110,178 A | 8/2000 | Zech et al. | |
| 6,110,209 A * | 8/2000 | Stone | 623/16.11 |
| 6,451,023 B1 * | 9/2002 | Salazar et al. | 606/86 |
| 6,530,928 B1 * | 3/2003 | Frei et al. | 606/99 |
| 6,588,992 B2 | 7/2003 | Rudolph | |
| 6,591,581 B2 | 7/2003 | Schmieding | |
| 6,592,588 B1 | 7/2003 | Bobic et al. | |
| 6,808,182 B2 * | 10/2004 | Lin | 279/74 |
| 6,857,830 B2 | 2/2005 | Holcomb | |
| 2002/0032447 A1 | 3/2002 | Weikel et al. | |
| 2002/0099382 A1 | 7/2002 | Salazar et al. | |
| 2002/0099383 A1 | 7/2002 | Salazar et al. | |
| 2002/0111632 A1 | 8/2002 | Lechot | |
| 2002/0157676 A1 | 10/2002 | Schmieding | |
| 2002/0188353 A1 | 12/2002 | Philippon | |
| 2002/0193802 A1 | 12/2002 | Zdeblick et al. | |
| 2003/0055431 A1 | 3/2003 | Brannon | |
| 2004/0034437 A1 | 2/2004 | Schmieding | |

FOREIGN PATENT DOCUMENTS

| | | |
|---|---|---|
| EP | 0495487 A2 | 7/1992 |
| WO | 9106246 | 5/1991 |

OTHER PUBLICATIONS

John C. Garrett; "Osteochondritis Dissecans"; Clinics in Sports Medicine; vol. 10, No. 3; Jul. 1991; pp. 569-593.

H.K. Outerbridge, et al; "The Use of a Lateral Patellar Autologous Graft for the Repair of a Large Osteochondral Defect in the Knee"; The Journal of Bone and Joint Surgery; vol. 77-A, No. 1; Jan. 1995; pp. 65-72.

G.E. van Dyk, et al; "Cancellous Bone Grafting of Large Osteochondral Defects: An Experimental Study in Dogs"; Arthroscopy: The Journal of Arthroscopic and Related Surgery; vol. 14, No. 3; Apr. 1998; pp. 311-320.

Innovasive COR.TM. System, Innovasive Devices, Inc., Jan. 1997.
Innovasive COR.TM. System: An Arthroscopic Technique for Harvesting and Transplanting Bone Grafts, Innovasive Devices, Inc., pp. 1-4, Sep. 1996.
N. Gould, "Trephining Your Way," Orthopedic Clinics of North America, vol. 4, No. 1, pp. 157-164 (Jan. 1973).
V. Bobic, "Arthroscopic osteochondral autograft transplantation in anterior cruciate ligament reconstruction: a preliminary clinical study," Knee Surg. Sports Traumatol, Arthroscopy, vol. 3, pp. 262-264 (1996).
L. Hangody et al., "MosaicPlasty.TM. Osteochondral Grafting Technique Guide," Smith & Nephew Endoscopy brochure (1996).
C. Fabbriciani et al., "Osteochondral Autograft in the Treatment of O.D. of the Knee," Orthopaedic Clinic, Catholic Univ., Rome, Italy (1996).
Y. Matsusue, "Arthroscopic Multiple Osteochondral Transplantation to the Chondral Defect in the Knee Associated with Anterior Cruciate Ligament Disruption," Arthroscopy, 9(3), pp. 318-321 (1993).
F. Yamashita, "The Transplantation of an Autogeneic Osteochondral Fragment for Osteochondrtis Dissecans of the Knee," Clinical Orthopaedics, No. 201, pp. 43-50 (Dec. 1985).
M. Brittberg et al., "Treatment of Deep Cartilage Defects in the Knee with Autologous Chondrocyte Transplantation," New England J. Med., vol. 331, No. 14, pp. 889-895 (Oct. 6, 1994).
V. Bobic, "Arthroscopic Osteochondral Autograft Transplantation in Chronic Anterior Cruciate Ligament Reconstruction," ESSKA 96, (1996).
V. Bobic, "An Update on Arthroscopic Osteochondral Autograft Transplantation in ACL Reconstrction," AOSSM 22nd Annual Meeting, (1996).
V. Bobic, "Arthroscopic Osteochondral Autograft Transplantation in Anterior Cruciate Ligament Reconstruction: A Preliminary Clinical Study," J Bone Joint Surgery >BR!, vol. 78-B: Supp. 1 (1996).
Mankin et al., Restoration of the Osteoarthrotic Joint, J Bone Joint Surgery, vol. 78-A, No. 1, pp. 1-2 (Jan. 1996).
J. Buckwalter, "New Methods of Treating Chondral Defects in the Knee" (undated).
L. Hangody, "Autologous osteochondral mosaic-like graft technique for replacing weight-bearing cartilage defects," ESSKA 96, Budapest, Hungary (May 10-15, 1996).
"Bone Dowel Harvester", Arthrotek, Inc., Copyright 2003.
Malinn, M.D., et al, Hypothermic Storage and Cryopreservation of Cartilage, (on or about Dec. 20, 1984).
Malinin, M.D. et al., Articular Cartilage Nutrition is Mediated by Subchondral Bone: A Long-Term Autograft Study in Baboons, Osteoarthritis and Cartilage Journal of the Osteo Arthritis Research Society Inernational, (2000).
Malinin, M.D. et al., Human Cadaver Femoral Head Homografts for Anterior Cervical Spine Fusions, (Reprinted from Surgical Neurology, vol. 7. No. 4, Apr. 1997).
Malinin, University of Miami Tissue Bank: Collection of Postmortem Tissues for Clinical Use and Laboratory Investigation, (Transplantation Proceedings, vol. VIII, No. 2, Supplement 1, Jun. 1976).
Acufex Microsurgical, Inc., Endoscopic Technique for ACL Reconstruction with Pro-Trac Tibial Guide: Endobutton Fixation, available by 2000.
Arthrotek, Inc., Autogenous Bone Coring: A Scientific Approach, 2004.
Arthrex, Osteochondral Autograft Transfer System (OATS), Surgical Technique, 1996.
Christel, P., Osteochondral Grafting Using Mosaicplasty Technique, printed Mar. 23, 2005.
Arthrotek®, Osteochondral Defect Surgical Technique, 1999.
Instrument Makar, Inc., Bone Grafters Surgical Technique, Dec. 1995.
Instrument Makar, Inc., New Directions in Arthroscopic Innovation, 1991 Catalogue.
Techniques for ACL Reconstruction with Multi-Trac™ Drill Guide, available by 2000.

* cited by examiner

METHOD AND APPARATUS FOR CORING AND REAMING OF BONE

FIELD

The present invention relates generally to orthopedic implants and procedures, and particularly to methods and apparatii for forming a core in a selected bone and harvesting a core from a selected bone.

BACKGROUND

In an anatomy, such as a human anatomy, various portions of the body are interconnected through soft tissues. For example, ligaments interconnect various boney portions of the anatomy to provide selected articulations of adjacent bone portions. The ligaments generally are attached or inserted naturally in the bone portions to provide tension to form the articulations and actions of the bones.

Nevertheless, over time the soft tissue, such as the ligaments, may become weakened or severed. The injuries may occur for various reasons, such as injury, fatigue, age, disease and other various reasons. The detachment of the ligament from its anatomical position reduces or eliminates the anatomical movement of the various bone portions.

If a ligament becomes detached, it may generally be repaired or replaced with a graft implant. Generally, a graft may be autogenus or zenographic. The graft may be implanted to interconnect the bone portions to substantially mimic the anatomical connection. The graft may be inserted or mechanically fixed to the bone portions. Nevertheless, it is desirable to increase pull out strength and increase bone regrowth after the implantation.

SUMMARY

A method and apparatus for providing a soft tissue implant to be fixed to a bone portion. The apparatus is used to form a bore in the bone to receive the graft. An autogenus or autograft of hard or cancelus bone tissue can then be positioned in the bore to seat the graft in the bore formed in the bone. Various supplementary fixation devices, such as a washer lock, described in U.S. Pat. No. 6,280,472 entitled "Apparatus And Method For Tibial Fixation Of Soft Tissue", commonly assigned, can also be used to fix a soft tissue in a selected position. The autogenus bone graft can be taken from the patient into which the soft tissue graft is being positioned. This can reduce or eliminate rejection of the graft. Also, the bone graft can assist in quicker healing by including most generally present proteins and normal anatomical portions to allow for bone in-growth, fixation, and other advantages.

A corer or harvester is provided to form the bore in the bone portion and allow for the harvesting of other substantially similar or complementary bone or autogenus implant. The bore formed in the bone is generally formed with a reamer of a selected diameter. A coring apparatus can be used to form a core or a bone plug substantially equal in diameter to the reamed bore. Therefore, after the bore is reamed in the bone, the selected tool can be used to form a core of a substantially similar diameter to the reamed or cored bore. Therefore, the bone plug, or core, can be positioned in the reamed or cored bore to assist in holding the soft tissue within the bore.

According to an embodiment an apparatus for harvesting a bone core is described. The apparatus includes a collet assembly having a sleeve defining an internal bore and a collar disposed within the internal bore wherein the collar is moveable, within the sleeve, between an engaged position and a non-engaged position. The apparatus further includes a chuck engageable member extending from the collet assembly to interconnect a selected chuck and a harvesting member selectively engageable with the collet assembly. The harvesting member is able to move the collar between the engaged position and the non-engaged position. When the harvesting member has moved the collar to the engaged position the harvesting member is selectively held within a portion of the internal bore. The harvesting member is able to move the collar generally with a manual force.

According to various embodiments an apparatus for harvesting and implanting a bone core includes a collet assembly having a selectively engageable mechanism and defining an internal bore. A harvester to selectively engage the selectively engageable mechanism and to be disposed within the internal bore, the harvester defining a harvester bore. Also, a graspable assembly to selectively engage the collet and defining a graspable assembly bore that is generally aligned with the harvester bore when the graspable assembly selectively engages the collet assembly. A plunger may be disposed within the graspable assembly bore and the harvester bore. The plunger is operable with the harvester bore during a harvesting of the bone core. The collet is disengageable from the graspable assembly and the plunger is operable to remove the bone core from the harvester. The selectively engageable mechanism includes a generally quick-release mechanism wherein the harvester is engageable and disengageable from the selectively engageable mechanism with pressure from the user.

According to another embodiment a method of harvesting and implanting a bone core includes interconnecting a harvesting member with a collet member in a quick-release manner and interconnecting the collet and a graspable member. The harvesting member is driven into a selected bone portion and traps a selected length of bone within the harvesting member. The selected length of bone is removed from the harvesting member into a selected location.

Further areas of applicability will become apparent from the detailed description provided hereinafter. It should be understood that the detailed description and specific examples, while indicating the various embodiments are intended for purposes of illustration only and are not intended to limit the scope of the appended claims.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit various applications or uses. Although the following description relates generally to a ligament replacement in a knee portion, such as an ACL replacement, it will be understood that the various methods and apparatuses may be used in any appropriate procedure or any type of soft tissue replacement. For example, a tendon may also be replaced in an elbow joint, shoulder joint, or other appropriate joint. In addition, it may be desirable to form a reamed portion or a bore and provide therein a core of selected bone portion. Therefore, the replacement of a tendon or a ligament is not necessarily a requirement of the following apparatuses or methods. The apparatuses and methods may be augmented to provide for various or similar procedures without being outside of the scope of the following description and the appended claims.

Figure 1:
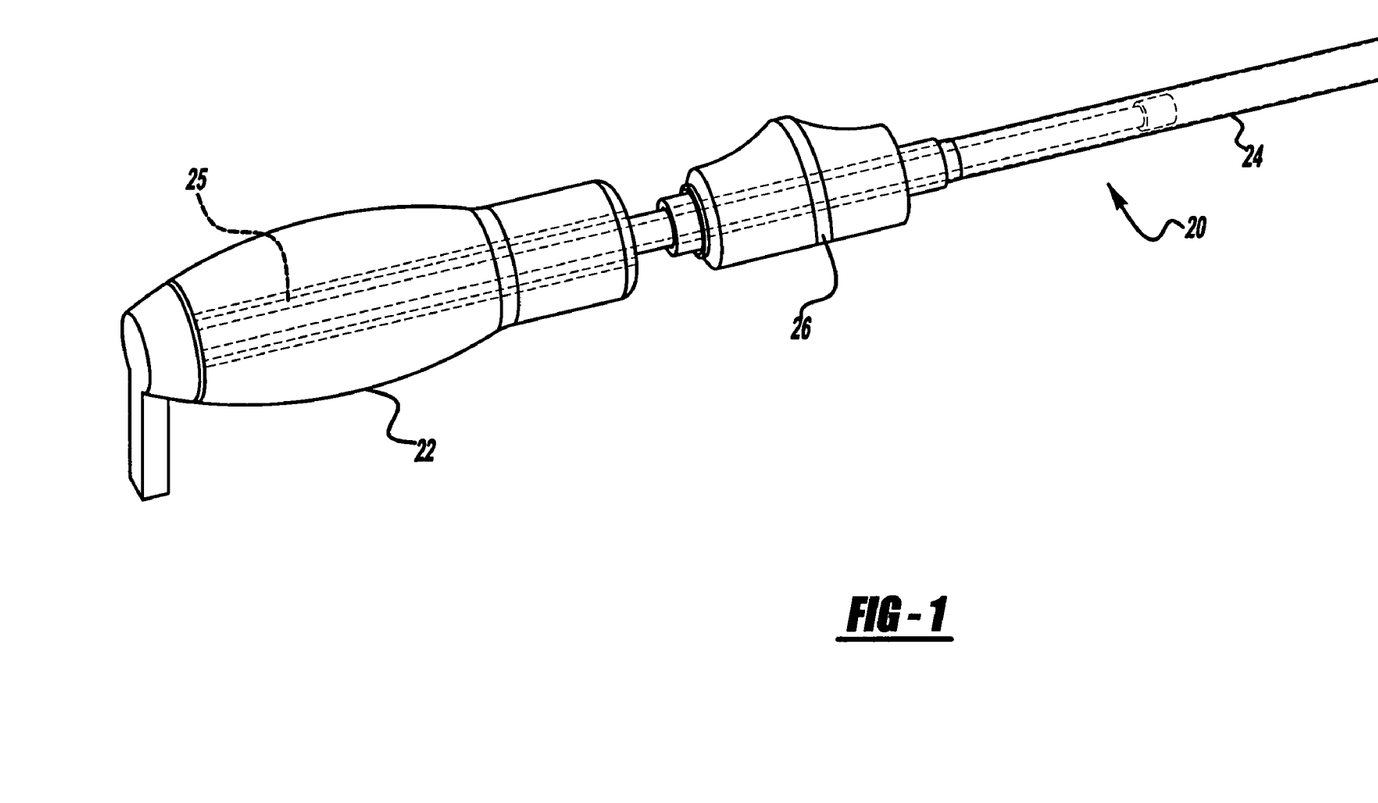
FIG. 1 is a perspective view of a coin instrument according to an embodiment.

With reference to FIG. 1, a harvesting instrument 20 according to an embodiment is illustrated. The harvesting instrument 20 generally includes an impact handle 22, a coring or harvesting member 24, a plunger 25, and a quick-release collet 26. As described in further detail herein, the quick-release collet 26 can be selectively affixed to the handle 22 and also quick releasingly engages the harvesting member 24. The quick-release collet 26 can also be used to engage a reamer, as further described herein. Nevertheless, the coring instrument 20 can be used to core a selected boney portion in a selected procedure.

Figure 2:
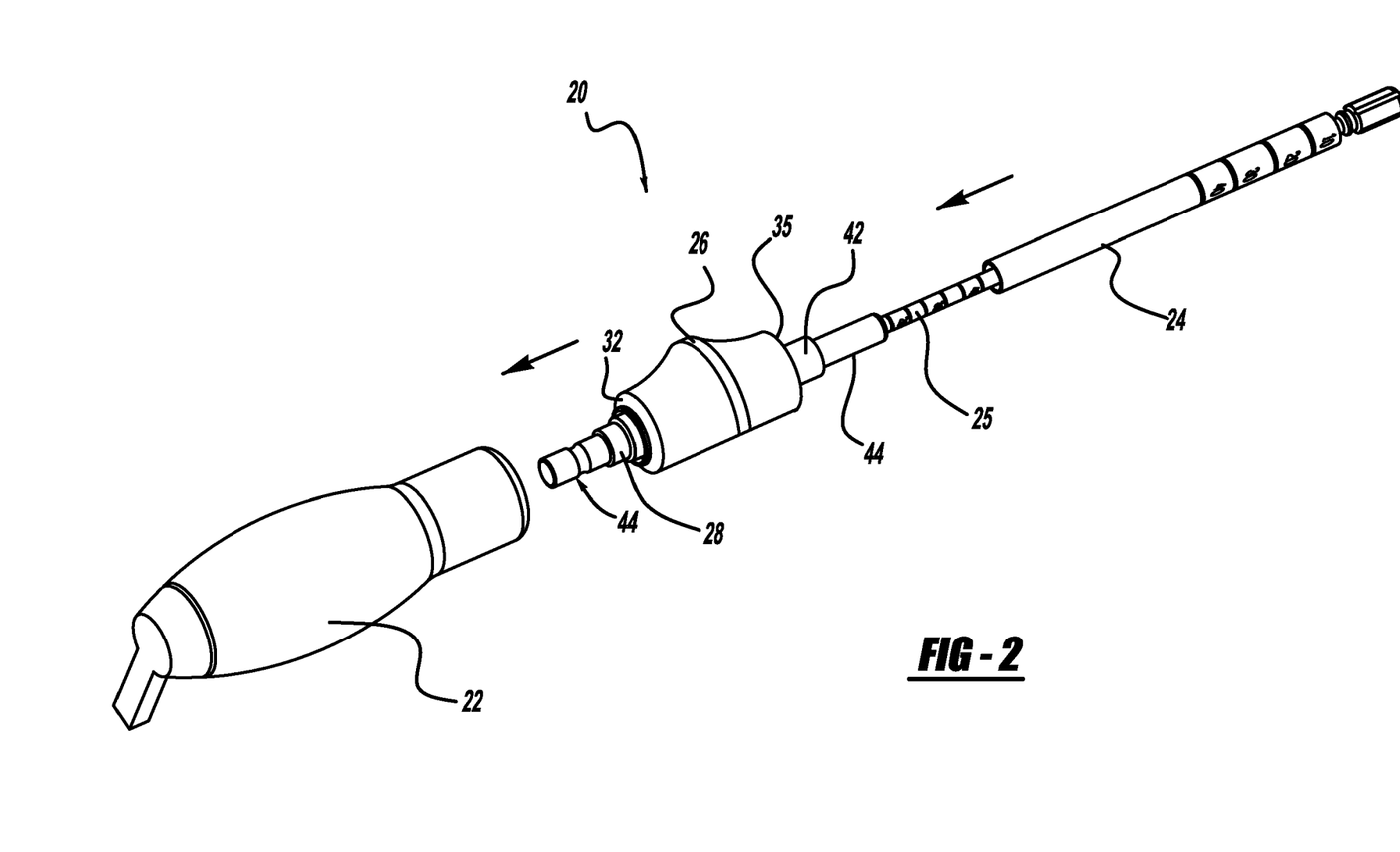
FIG. 2 is an exploded view of the instrument in FIG. 1.
Figure 3:
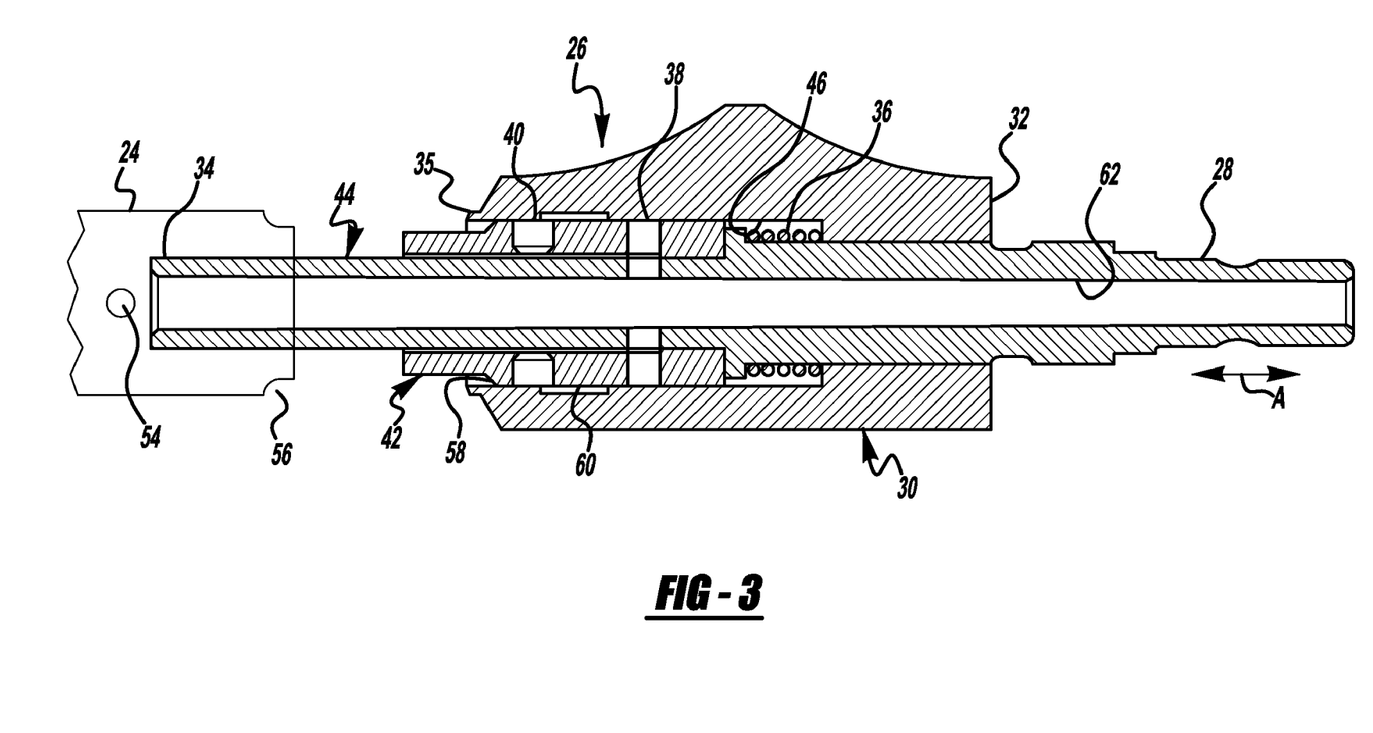
FIG. 3 is a detailed cross-sectional view of a quick-release portion of the instrument.

With reference to FIGS. 2 and 3, each portion of the instrument 20 may be dismantled or disassembled from the other portion. That is, the handle 22 is generally removably connected to the collet 26 with an appropriate mechanism. The collet 26 includes a engageable portion or chuck engageable member 28. The chuck engageable member 28 is generally received within a sleeve 30 of the collet 26. The chuck engageable portion 28 extends from a first or proximal end 32 of the sleeve 30 while a second end or tool engageable portion 34 of the collet 26 extends from a distal end 35 of the collet 26.

The tool engageable portion 34 generally engages a selected portion of a tool such as the harvesting member 24. Therefore, each of the portions, the handle 22, the collet 26 and the harvesting member 24 may be disengaged at a selected time. This allows for the collet 26 and the harvesting member 24 to be removed from the handle 22 after the selected core is taken, as described herein. In addition, it allows for the harvesting member 24 to be used with any appropriate graspable member rather than only the handle 22.

Nevertheless, the chuck engageable portion 28 allows the handle 22 to securely engage the collet portion 26 for manipulation of the harvesting member 24.

The collet 26 may be generally triangular in shape. This allows for easy manipulation by user, such as a surgeon, during the use of the instrument 20. Nevertheless, it will be understood that the collet 26 may be any appropriate shape, such as generally cylindrical and include portions that are knurled to allow for easy manipulation of the instrument.

With further reference to FIG. 3, the collet 26 may be a quick-release collet. Although the chuck engageable portion 28 may be substantially permanently or selectively engaged in a selected tool, the distal portion 35 of the collet 26, including the portions included therein, are designed to allow for a generally substantially quick-release of the tool, such as the harvesting member 24 from the collet 26. Therefore, the harvesting member 24 may be pressed into the collet 26 and held therein for a use without the need of other manipulation.

To this end, the internal mechanisms of the collet 26 may be any generally known quick-release mechanism. The following is merely exemplary, and not intended to limit the scope of the appended claims. An exemplary quick-release mechanism may include a compression spring 36, a dowel pin 38, a ball bearing 40 which are generally housed within or interact with collar 42.

The chuck engageable portion 28 and the tool engaging portion 34 are generally integrally formed as a single unit. Nevertheless, it will be understood that they may be formed of two or more portions. Regardless, the chuck engageable portion 28 and the tool engaging portion 34 generally define a member 44 that is held within or interacts with the collar 42. The collar 42 may be held or secured within a central chamber or bore 46 formed within the sleeve 30. The compression spring 36 allows for the collar 42 and the member 44 to move axially in the direction of arrow A relative to the sleeve 30. The compression spring 36 biases the member 44 towards the distal end 35 of the collet 26 prior to insertion of the harvesting member 24. As described herein, pressure from insertion of the harvesting member 24 into the distal end 35 of the collet 26 moves the collar 42 and allows for interaction of the pin 38 and the bearing 40 to generally interconnect the harvesting member 24 with the collet 26 and in turn the handle 22.

Figure 4A:
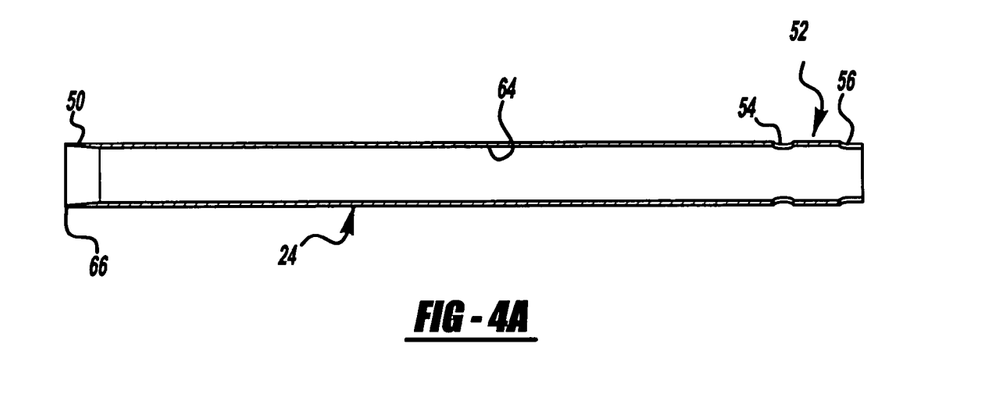
FIG. 4A is a cross-sectional view of a coin member.
Figure 4B:
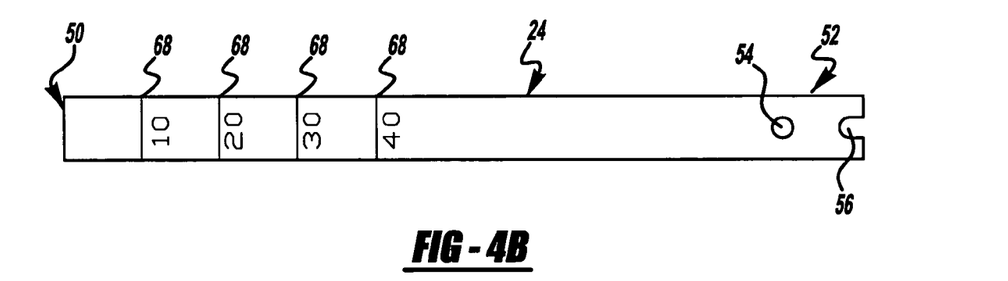
FIG. 4B is a plan view of a coin instrument according to FIG. 4A.

The harvesting member 24, with reference to FIGS. 4A and 4B, generally defines a coring or sharpened end or portion 50 and a collet engaging end 52. The collet engaging end 52 generally includes openings or apertures 54 that are able to engage selected portions of the collet 26, such as the bearings 40. An additional aperture 56 is provided to engage the pin 38 within the collar. Therefore, as the harvesting member 24 is passed over and may encompass at least a portion of the tool engaging portion 34, the pin engaging portions 56 are able to engage the pin 38 and the bearing apertures 54 are generally engaged by the bearings 40.

The pin engaging portions 56 allow for the pin 38 to interact with harvesting member 24 such that a torque may be passed from the collet portion 26, or from the chuck engaging member 28 to the harvesting member 24. The bearing apertures 54, in addition and alternatively to the pin 38, interact with the bearings 40 to assist in alignment of the harvesting member 24 with the collet 26. As the harvesting member 24 is pressed over to encompass at least a portion of the collar 42, it engages a shoulder or coring engaging portion 58 to press the collar 42 towards the proximal end 32 of the sleeve 30. As this occurs, the bearings 40 are able to pass through the bearing apertures 54 and engage a bearing locking depression 60 formed within the sleeve 30. At this position, the bearings are generally able to hold the collar 42 in a selected position relative to the sleeve 30 which, in turn, holds the harvesting member 24 in the selected position relative to the sleeve 30 for the operation of the harvesting member 24. The compression spring 36 provides tension to the mechanism to allow for the bearings 40 to generally engage and hold the mechanism in a selected position. Nevertheless, the bearings 40 are generally allowed to move a distance and may further include a compression spring held near the bearing 40. With the application of a selected force, such as pulling the harvesting member 24 towards the distal end 35 of the sleeve 30, the bearings 40 may disengage from the depression 60 to allow for removal of the harvesting member 24 from the collet 26.

The member 44, including the chuck engageable portion 28 and the tool engaging portion 34 generally define a cannula 62. Similarly, the harvesting member 24 generally defines a cannula 64. The two cannula 62, 64 are generally aligned after forming the interconnection of the harvesting member 24 with the collet 26, for reasons described herein.

With additional reference to FIGS. 4A and 4B, the harvesting member 24 is generally elongated and is formed of a selected material that defines the internal cannula 64. The internal cannula 64 defined by the harvesting member that defines a tube 24 is substantially equal in diameter, or a selected distance, between the cutting end 50 and the collet engaging end 52. As an example, the internal cannula 64 being of a substantially equal distance throughout may allow any material positioned therein to be removed from either the cutting end 50 or the collet engaging end 52. Therefore, the material positioned therein can be removed if either of the two ends becomes damaged or blocked due to other reasons.

The cutting end 50 is generally tapered and includes a sharpened portion or cutting edge 66. The cutting edge 66 may be used to cut a selected portion, such as a selected bone portion. In addition, on an exterior of the harvesting member 24 may be demarcations 68 that may include any appropriate scale. For example, markings may be included at approximately 10 mm intervals such that markings at 10, 20, 30, 40 mm are provided on the exterior of the harvesting member 24. The demarcation 68 may be used to provide or select a length or depth of a core portion. A user may view the markings 68 on the exterior of the harvesting member 24 to determine the depth of the harvesting member 24 within the selected member. It will be understood, that the harvesting member 24 may be formed of any appropriate material. For example, various biocompatible metals may be used that may be easily formed and sharpened to form the sharpened edge 66. Various alternatives may also include ceramics and polymers.

Figure 5:
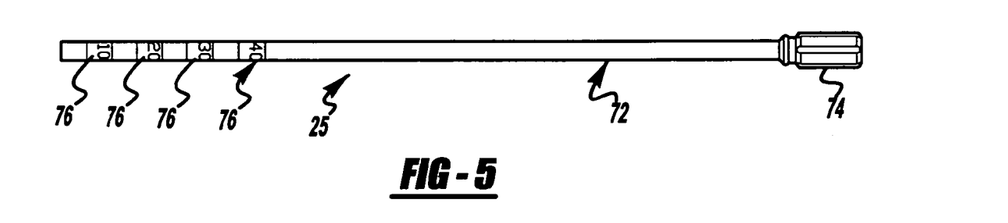
FIG. 5 is a plan view of a plunger for use within the coin instrument.

With reference to FIG. 5, the plunger 25 is illustrated. The plunger 25 generally includes a shaft 72 and a plunger end or portion 74. The plunger portion 74 is generally similar in exterior diameter to the interior diameter of the cannula 64 defined by the harvesting member 24. The shaft 72 may be any appropriate size, but is generally sized to allow for a rigid interaction with the plunger portion 74 and any harvested or selected bone portion. In addition, the harvester shaft 72 may be bent or sized to provide for an interference fit with the member 44 within the collet 26. The shaft portion 72 of the plunger 25 may pass through the cannula defined by the handle 22, the collet 26, and the member 44 including the chuck engageable portion 28 and the tool engageable portion 34. In addition, the plunger shaft 72 may also include markings 76 to provide for an indication to a user. Again, the markings 76 may be provided at any appropriate definition, such as 5 or 10 mm. As described herein, the markings 76 allow a user to determine the length of a core or harvested portion that is harvested or being positioned back into a body.

Figure 6:
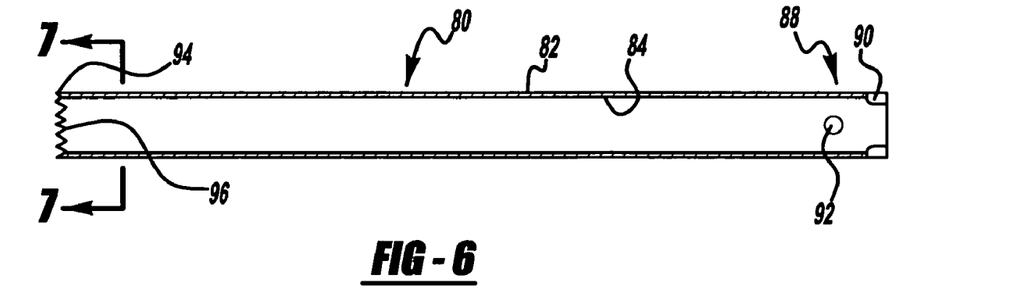
FIG. 6 is a cross-sectional view of a coin instrument according to an alternative embodiment.
Figure 7:
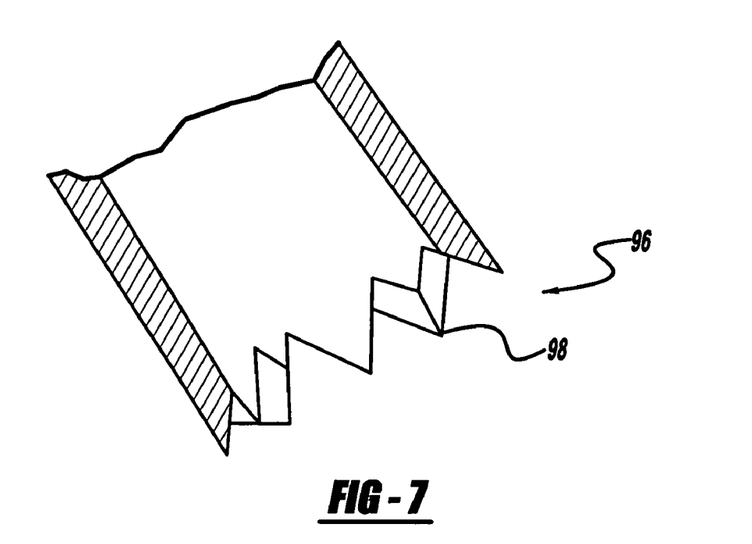
FIG. 7 is a detailed cross-sectional view of a cutting end of the coin instrument according to FIG. 6.

With references to FIGS. 6 and 7, a harvesting member 80 according to an alternative embodiment is illustrated. The harvesting member 80 generally includes an extended body portion 82 that defines a cannula 84. As discussed above in relation to the tube 64, the cannula 84 of the tube 80 may be substantially equal in a dimension, such as a diameter, between the cutting or distal end 94 and the collet engaging end 88. A proximal end of the harvesting member 80 includes a collet engaging end 88 that defines a pin engaging portion 90 and bearing engaging apertures 92. The harvesting member 80 also defines a distal end 94 that includes a cutting portion 96. The cutting portion 96 defines a plurality of cutting teeth 98. The cutting teeth 98 may be defined in any appropriate manner such that they may be rotated to harvest a selected portion of bone. Therefore, the harvesting member 80 can be rotated to harvest a selected portion of bone which can be collected within the cannula 84 defined by the shaft portion 82. It will be understood that markings, such as depth markings, may also be included on the exterior of the harvesting member 80.

The harvesting member 80 may be rotated by a selected tool, such as a drill or other commonly known rotating apparatus. Therefore, the harvesting member 80 is not necessarily used with the handle 22, but may be used with a cannulated drill. Nevertheless, the collet 26 can engage the pin apertures 90 and the bearing apertures 92 while the chuck engaging portion 28 of the collet 26 engages a chuck of a tool or drill. Therefore, the harvesting member 80 can be used in addition or alternatively to the harvesting member 24 to create a selected core portion, but still with the quick-release collet 26.

It will be understood that various changes may be made to the tools described above to perform a selected reaming and coring apparatus or method. The following method, described with reference to FIGS. 8-13, may be followed with the instruments described above. Nevertheless, it will be understood that any appropriate method may be used to provide a selected core for a selected procedure. In addition, although the following description relates generally to a method to perform an ACL replacement, it will be understood that the instruments may be used for any appropriate method and the method may be altered depending upon selected portions which are being cored and implanted.

Figure 8:
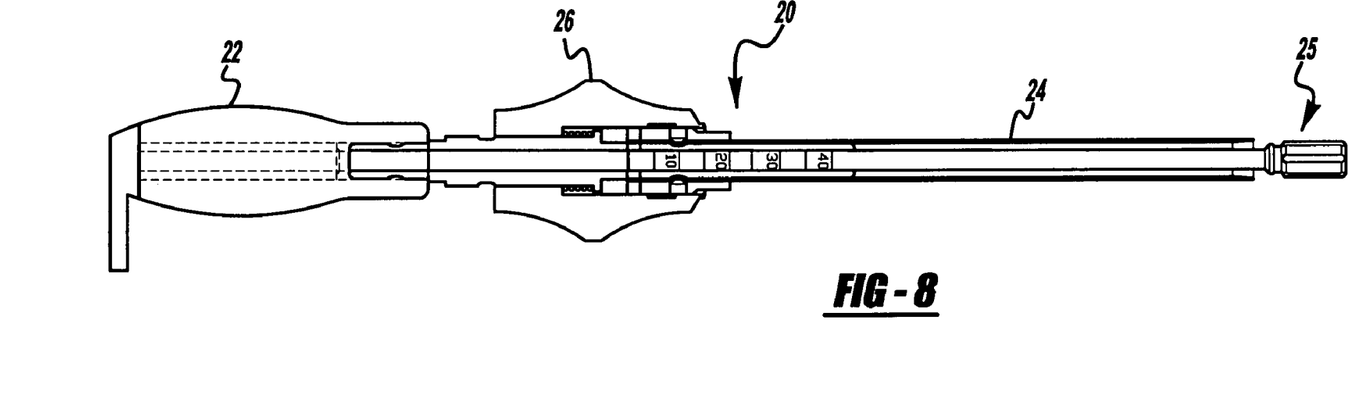
FIG. 8 is a partial cross-sectional view of the instrument in FIG. 1 assembled.
Figure 8A:
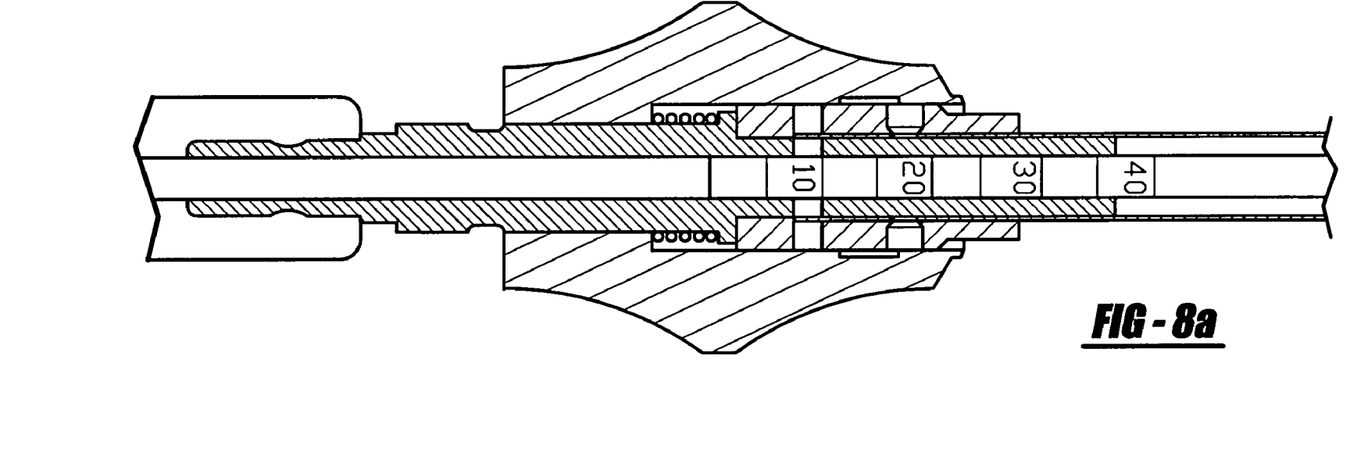
FIG. 8A is a partial cross-sectional detailed view of a quick-release portion of the assembled instrument.

With initial reference to FIG. 8, the instrument 20 is first prepared for use by interconnecting the handle 22 with the collet 26 and the harvesting member 24. In addition, the plunger 25 is positioned through the cannula defined by the harvesting member 24, the collet 26, and the handle 22. The plunger 25 may be designed such that a portion of the shaft 72 extends from the proximal end of the handle 22 before insertion or does not extend at all. Generally, when the harvesting member 24 is provided, the handle 22 is used as a striking surface to force the harvesting member 24 into the bone to be cored. Therefore, providing the plunger 25 to extend through the handle 22 may disrupt the ability to strike the proximal end of the handle 22.

Figure 9:
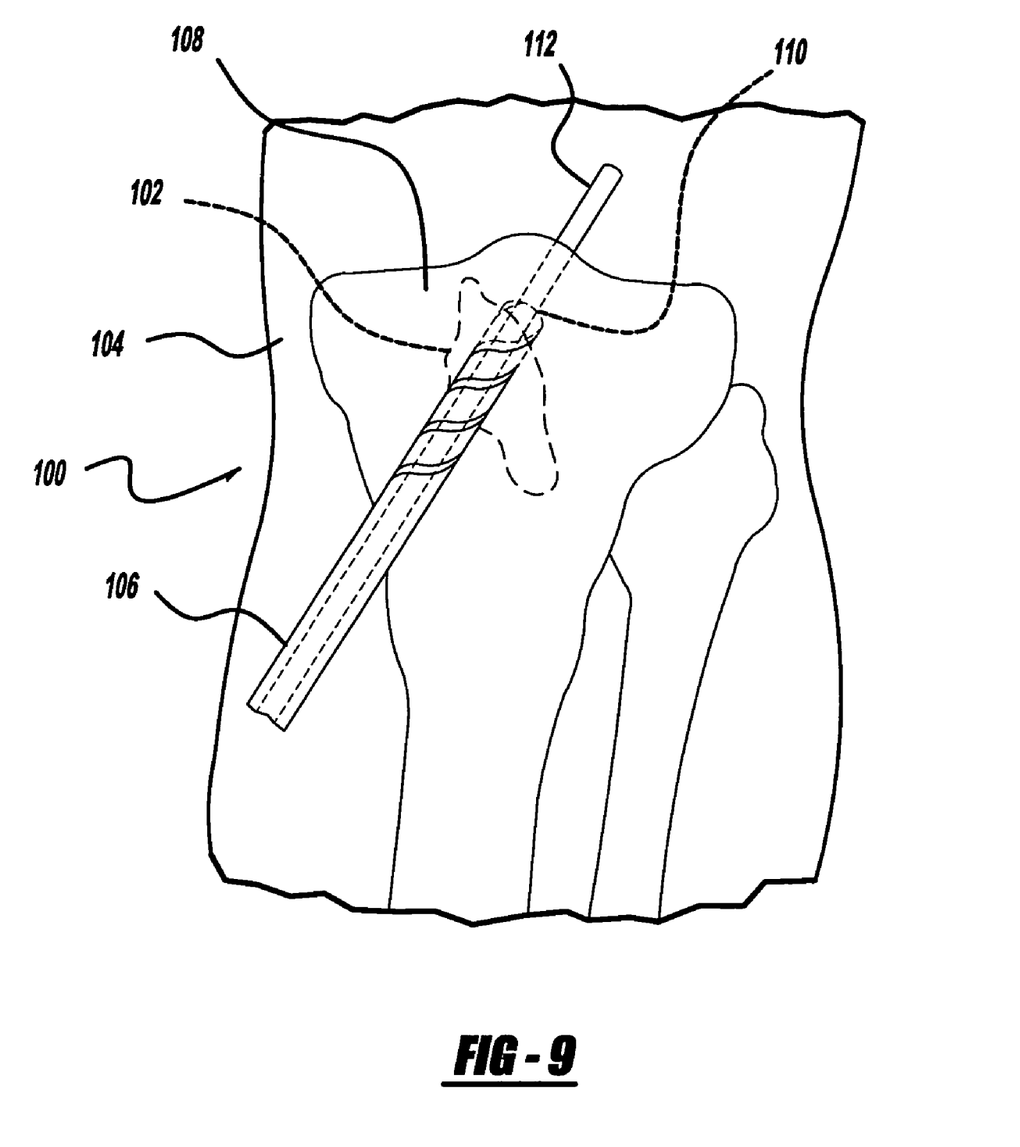
FIG. 9 is an environmental view of a knee joint being reamed.

With reference to FIG. 9, an exemplary procedure may include an anterior cruciate ligament (ACL) reconstruction. As discussed above, an ACL construction is simply exemplary as the general process described herein can be used to remove a bone core from any selected portion of the anatomy, such as from the femur, from a humerus, or any other appropriate bone portion. In addition, the bone core may be removed from any appropriate bone portion and positioned in the appropriate bone portion for any selected procedure and not simply only an ACL reconstruction. Therefore, a selected knee joint 100 can be first prepared for the procedure. First, an incision 102 may be formed in the soft tissue 104 surrounding the knee joint. After the incision 102 is formed, a reamer 106 may be used to ream a selected portion of a tibia 108. Appropriate reamers 106 are generally known and need not be described in detail herein. Also, techniques for guiding and providing a bore 110 formed by the reamer are also generally known and not described in detail herein. One generally skilled in the art will understand the various methods that may be used to form the bore 110 in addition to the methods described herein. According to one embodiment, the reamer 106 may be used to ream through the cortex bone of the tibia 108.

The reamer 106 may only provide a bore through the cortex bone prior to the use of the instrument 20. It will also be understood that the instrument 20 may be used to form a bone core in any appropriate location. Although the following description describes providing a bore formed using the instrument 20 relative to a bore formed by the reamer 106, it will be understood that a bone core may be harvested from any appropriate bone portion and is only exemplary described to be removed from the tibia. Thus, the reamer 106 may form the entire bore 110 through which the soft tissue graft will be passed. In addition the instrument generally forms a bone core including substantially bone material. Therefore, the reamer 106 may ream both the initial portion of the bore 110 and the final portion to ensure that the bone core consists substantially of bone.

Nevertheless, the reamer 106 may also remove the distal end of the bore 110 therefore the instrument 20 only removes a portion of the cortical bone to form a portion of the bore 110. That is, that the instrument 20 may produce a bone core including any appropriate portion or selection of bone material while a separate instrument, such as the reamer 106, may be used to remove other portions of the anatomy, such as the soft tissue adjacent the bone core being removed.

It will also be understood that the incision 102 may be any appropriate size, but is generally between about 1 cm to about 10 cm. Therefore, the procedure may be augmented with an arthroscope that is either passed through the incision 102 or other appropriate incisions. Nevertheless, the reamer 106 may be guided with a guide wire 112 over which the instrument may also pass. Therefore, the guide wire 112 may be used to guide the coring instrument 26 as it passes into the tibia 108 to harvest a core therefrom.

Figure 10:
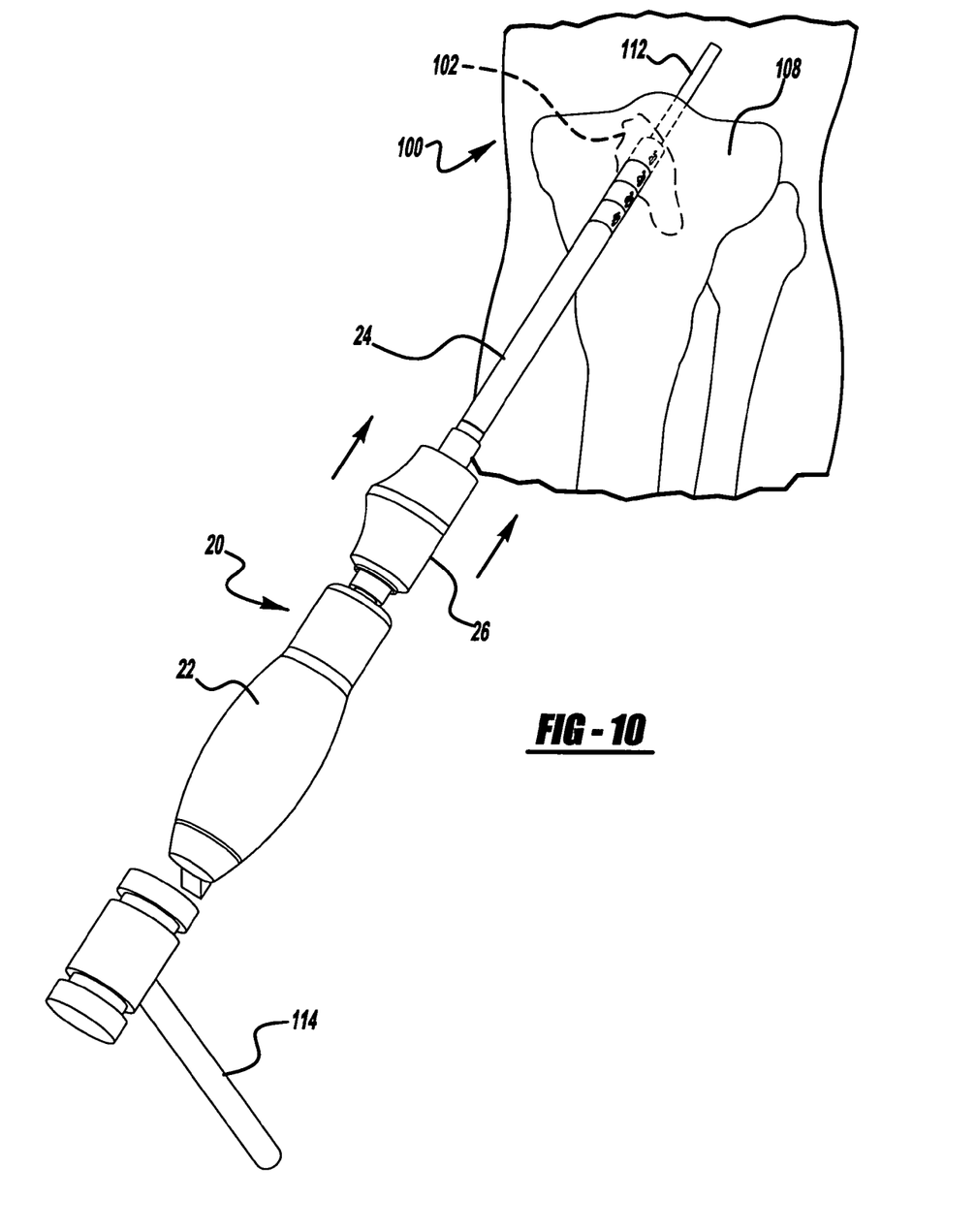
FIG. 10 is an environmental view of the coin instrument according to a method of use.

The instrument 20 may be used to harvest a core by positioning the coring instrument 20 relative to the tibia 108 and striking a proximal end of the handle 22 with a mallet or other appropriate instrument 114. The instrument 20 may be struck several times to provide a core of a selected depth. As discussed above, the markings on the exterior of the coring instrument 20 may be used to determine the depth at which the harvesting member 24 has penetrated the tibia 108. The markings may be viewed either through the incision 102 or through a selected arthroscope or other viewing instrument. In addition, the markings may be radio opaque so that a fluoroscopy or other appropriate techniques may be used to view the depth indications on the harvesting member 24. After the harvesting member 24 has passed the selected distance into the tibia 108, the harvesting member 24 may be loosened or removed from the bone by rotating the instrument 20. A rotation may break off the core portion that is positioned within the cannula 64 defined by the harvesting member 24.

As mentioned above, the instrument 20 is able to form the bore 110 through which the soft tissue graft may be passed to provide for the interconnection of the selected bone portions. Therefore, as the core is harvested from the tibia 108 with the harvesting member 24, the harvesting member 24 is also forming the bore 110. Although the reamer 106 forms an initial portion of the bore 110, the harvesting member 24 provides the final bore 110 by removing the selected core portion. It is this core portion that may be replaced into the bore 110 at a selected time, as described herein. Nevertheless, the bore 110 may be formed entirely with the reamer 106 and a selected bone core harvested from an alternative area to be replaced into the bore 110. Therefore, it is not necessary to harvest the bone core from the bore 110 but may be harvested from any appropriate location.

It will be understood that as the harvesting member 24 is driven into the tibia 108, it substantially surrounds and collects within the cannula 64 a selected core portion. Therefore, the only portion of the bone core still attached to the tibia 108 is the portion at the distal end of the harvesting member 24 and rotating the instrument 20 may allow for removal of the instrument 20 from the tibia 108 while retaining the core within the harvesting member 24.

According to an alternative harvesting member 80 rotating core instrument 80 may be used to provide or harvest a core in a similar manner. Although, the rotating harvesting member 80 need not be struck with the mallet 114, it may be provided to obtain a core from a selected bone portion. Although not specifically illustrated, the rotating harvesting member 80 can be provided on a drill and guided with a guide wire 112 to harvest the core from the tibia 108. The sawteeth 98 are generally able to cut through the bone of the tibia 108 to provide a substantially clean cut of the bone and provide the core within the cannula 84 of the harvesting member 80. Also the use of the rotating harvesting member 80 may eliminate the need for initially reaming a selected portion of the tibia. That is, the sawteeth 98 of the harvesting member 80 may be able to pass through the cortex bone of the tibia 108. Nevertheless, it may be desirable to ream the cortex portion of the bone regardless such that it is not repositioned into the bore 110.

Figures 11, 11A:
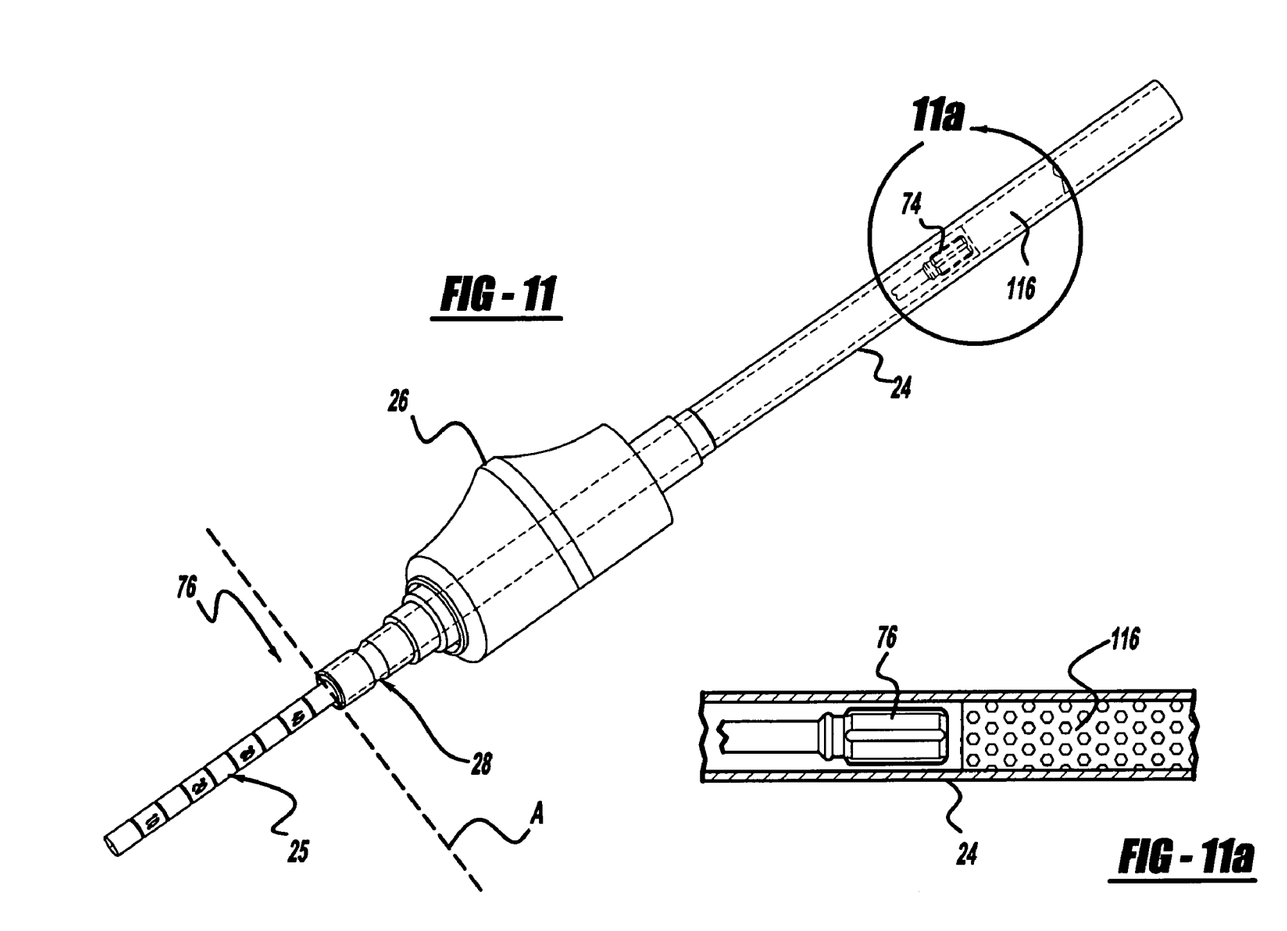
FIG. 11 is a perspective view of the coin instrument after a bone core is taken.
FIG. 11A is a detailed view of the bone core within the coin instrument.

With reference to FIG. 11, after the instrument 20 has been removed from the knee joint 100, the collet 26 may be removed from the handle 22 to reveal the plunger 25, and particularly, the shaft 72 thereof. The markings 76 can be read on the shaft 72 of the plunger 25 to assure that a selected length of a core 116 of the tibia 18 has been received. The markings 76 are generally read relative to a plane A which is defined by a proximal end of the chuck engageable portion 28. It will be understood that the markings 76 may be formed relative and read relative to any appropriate portion of the assembly or any other selected region, but is generally provided that the markings 76 may be read relative to the plane A. The core 116 of bone is trapped within the cannula 64 and the plunger portion 74 generally rests on an end thereof. Therefore, the markings 76 on the plunger 25 can verify the depth of the core 116 in addition to the markings formed on the exterior of the harvesting member 24.

Figure 12:
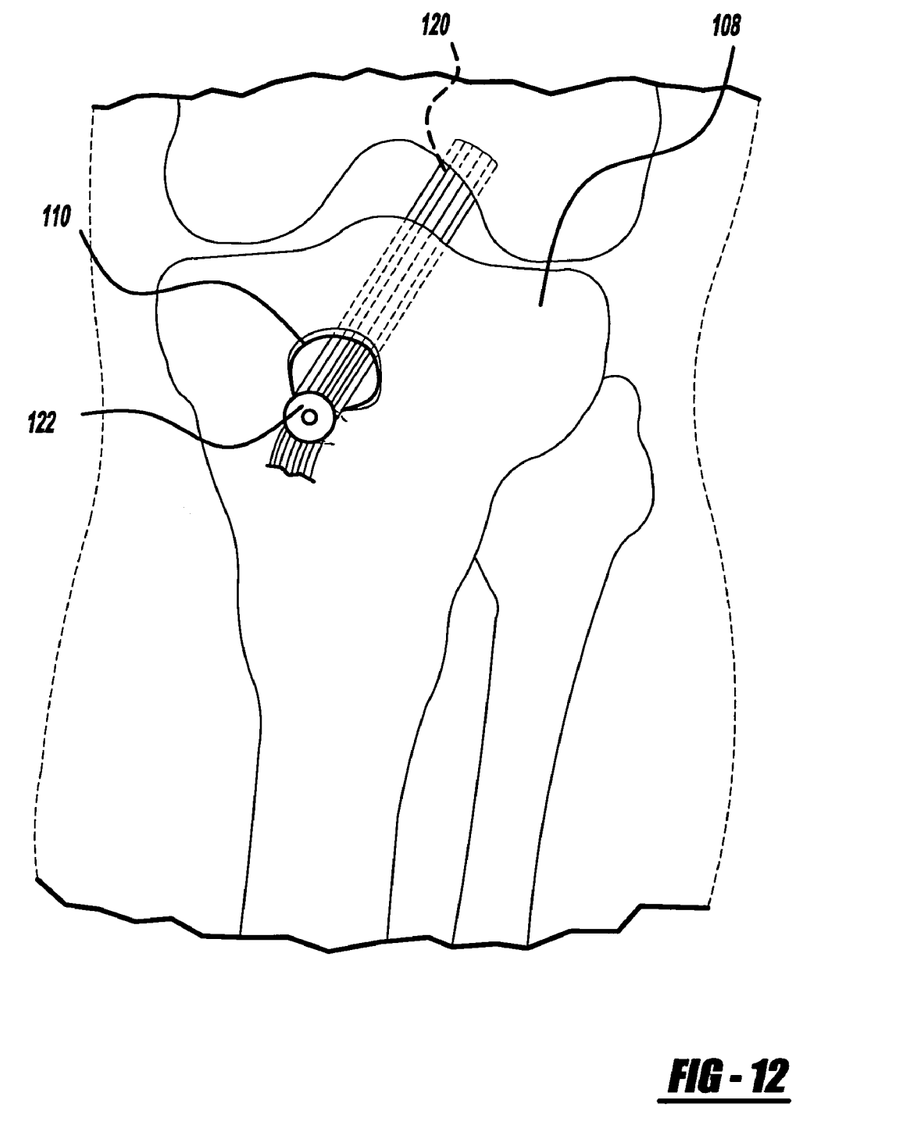
FIG. 12 is an environmental view of the soft tissue partially implanted in the knee joint.

With reference to FIG. 12, after the core 116 has been taken, the bore 110 is substantially completed. After this, a soft tissue graft 120 may be passed through the bore 110 according to appropriate and generally known techniques. In addition, the graft may be fixed to the tibia 108 with generally known techniques such as with a washer lock 122 described in U.S. Pat. No. 6,280,472 and commonly assigned, incorporated herein by reference. Therefore, the soft tissue graft 120 may be fixed to the tibia 108 through any appropriately or known techniques. Nevertheless, after the soft tissue graft has been fixed with the washer lock 122, or any other device to the tibia 108, the core 116 may be repositioned into the bore 110 to provide for additional fixation and assist in eliminating tunnel or bore dilation.

According to an embodiment, the bore 110 may first be dilated or enlarged from the diameter formed by the harvesting member 24. The end of the bore 110 is enlarged to allow replacement of the core 116 in a substantially easy manner. The bore 110 may be dilated through any appropriate technique, such as with an expander. Nevertheless, the bore 110 is generally enlarged just enough to allow for replacement of the harvesting member 20 and appropriate protecting portions, describing herein, into the bore 110 to allow for implantation of the harvested core 116.

Figure 13:
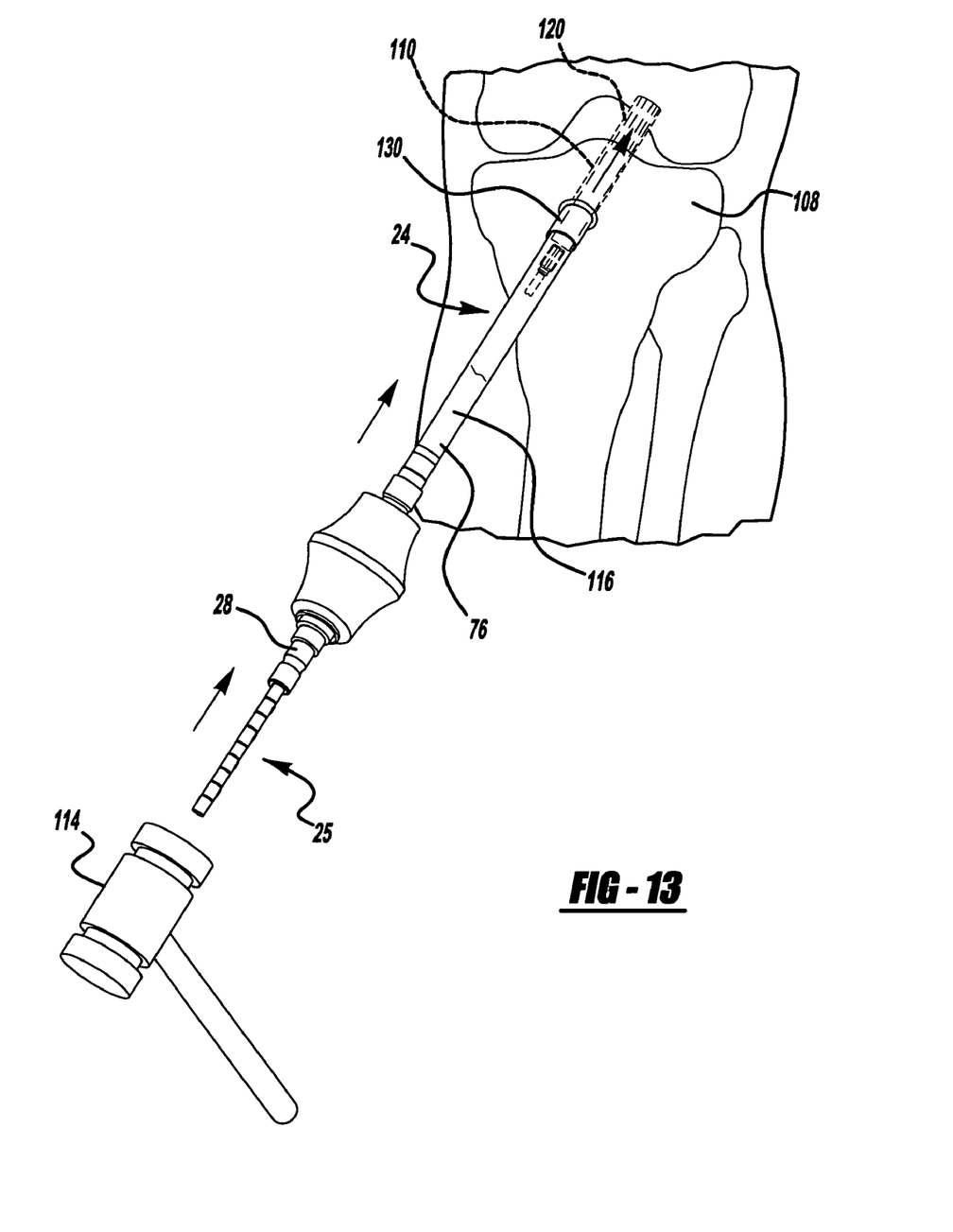
FIG. 13 is an environmental view of the replacement of a bone core according to an embodiment.

After the bore 110 has been dilated, bone chips, such as chips formed during reaming of the bore 110 may be provided and impacted in the bore 110. After this has occurred, the bone core 116 may be provided into the bore 110. With reference to FIG. 13, a protective sleeve 130 can be positioned over the cutting end of the harvesting member 24. This ensures that the harvesting member 24 does not again pass into the bore 110 or cut the soft tissue graft 120 that has been fixed to the tibia 108. In addition, the dilation of the bore 110 allows for the positioning of the protective sleeve 130 into the bore 110 and still allowing for the positioning of the harvesting member 24 relative thereto. After the protective sleeve 130 is positioned on the harvesting member 24, it may be positioned back into the bore 110, generally through the incision 102. The plunger 25 may then be used as a striking surface to be struck with the mallet 114 to force the bone core 116 out of the harvesting member 24 and into the bore 110. Therefore, the core 116 can be positioned back into the bore 110 from which it was removed to further fix the soft tissue graft 120 in the bore 110.

It will be understood that a generally friction fit between the core 116 and the tibia 108 is formed as it forced back into the bore 110. Nevertheless, additional fixation media can be used to assure a substantially permanent fixation between the core 116 and the bore 110. For example, additional screws and pins may be implanted to fix the bone therein or materials, such as bone cement or bone glue, may be used to further fix the core 116 in the selected position.

Nevertheless, the core 116 generally allows for a osteoinduction of bone back into the bore 110 to allow for a substantially permanent fixation of the soft tissue graft 120 in the bore 110. Therefore, the soft tissue graft 120 can provide for an interconnection of the fibia (not numbered) to the tibia 108. An ACL restruction can be performed using the soft tissue graft 120 and the core 116. Nevertheless, as discussed above, other appropriate methods may be performed with the instruments to provide for fixation of the selected soft tissue relative to a selected bone.

It will be understood that although the bone core 116 is illustrated to be positioned into the bore 110 defined by the tibia, it will be understood that the core 116 may be positioned into any appropriate portion. For example, even in the exemplary ACL replacement procedure, the bone core may be positioned into the femur to assist in fixation of the soft tissue graft therein. Alternatively, the bone core 116 may be positioned in any appropriate bone member depending upon the selected procedure. Furthermore, the bone core 116 may be taken from any appropriate bone portion and positioned in the bore 110 defined in the tibia. For example, it may be desired to form the bone core 116 from a portion of the femur and positioned in the bone core 116 in the bore 110 defined in the tibia. The bore 110 defined in the tibia may be defined by the instrument 20 or with the reamer 106 to provide for receiving the bone core 116. Therefore, it is understood that the above described procedure is simply exemplary of any appropriate procedure that may use a selected bone core.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An apparatus for harvesting and implanting a bone core, comprising:
    a collet assembly including a selectively engageable mechanism, said collet assembly further having a sleeve defining a sleeve throughbore, a collar disposed within said sleeve throughbore and having a collar throughbore, and a compression spring within said sleeve throughbore providing a biasing force on said collar;
    a harvester to selectively engage said selectively engageable mechanism and to be at least partially disposed within said sleeve throughbore and encompass a portion of said collar, said harvester defining a harvester throughbore;
    a first graspable assembly and a separate second graspable assembly to selectively engage said collet assembly, each defining a graspable assembly bore that is generally aligned with said harvester throughbore when said first or second graspable assembly are separately and selectively engaged to said collet assembly; and
    a pin extending from said collar to engage a proximal pin engaging depression in an end wall of said harvester such that as a torque is applied to said collet assembly the torque is transferred to said harvester;
    wherein said collar is slideable within said sleeve throughbore when acted upon by said harvester;
    wherein said collar is biased in a first position by said compression spring disposed between said collar and said sleeve;
    wherein said first graspable assembly is a drill motor and said second graspable assembly is a handle wherein either said drill motor or said handle individually selectively engages said collet assembly;
    wherein said selectively engageable mechanism includes a generally quick-release mechanism wherein said harvester is engageable and disengageable from said selectively engageable mechanism with pressure from the user.

2. The apparatus of claim 1, further comprising:
    a plunger moveable within said graspable assembly bore and said harvester throughbore;
    wherein said plunger is operable with said harvester throughbore during a harvesting of the bone core;
    wherein said collet assembly is disengageable from either of said first or second graspable assembly and said plunger is operable to remove the bone core from said harvester;
    wherein said collar throughbore, said sleeve throughbore, and said harvester throughbore are operable to be substantially coaxial.

3. The apparatus of claim 2, wherein the bone core is collectible within said harvester throughbore and said plunger is operable to remove the bone core from said harvester throughbore.

4. The apparatus of claim 2, wherein said plunger is able to push the bone core into a selected position from said harvester substantially directly from said harvester.

5. The apparatus of claim 4, wherein said harvester throughbore is substantially equal in at least one dimension throughout.

6. The apparatus of claim 1, wherein said harvester includes a collet engaging end and a harvesting end;
    wherein said harvesting end includes a sharpened portion to cut a selected portion of a bone to harvest the bone core;
    wherein said harvester is operable to collect the bone core within said harvester throughbore.

7. The apparatus of claim 6, wherein said sharpened portion includes at least one of a sawtooth and a generally planar edge.

8. The apparatus of claim 7, wherein said handle is a driveable handle that is operable to be struck to drive said generally planar edge of said harvesting member substantially axially into a surface and maintain the bone core within said harvesting member;
wherein said drill motor is operable to rotate said harvesting member with said sawtooth into a surface and maintain the bone core within said harvesting member.

9. The apparatus of claim 1, wherein the bone core may be removed from either of said collet engaging end or said harvesting end.

10. A method of harvesting and implanting a bone core, comprising:
interconnecting a harvesting member with a collet in a quick-release manner, including operably contacting said harvesting member with a biasing member and providing a biasing force on said harvesting member;
interconnecting said collet with a graspable member including a graspable handle or alternatively a drill motor;
driving said harvesting member into a selected bone portion;
trapping a selected length of bone within said harvesting member; and
removing said trapped selected length of bone from said harvesting member into a selected location at least by pushing said trapped selected length of bone from a throughbore defined at least through said harvesting member and said collet while said harvesting member is interconnected with said collet;
wherein interconnecting said collet with a graspable member includes selectively locking said collet to said graspable handle that is strikeable with a mallet and driving said harvesting member includes striking said graspable member with said mallet to drive said harvesting member into the selected bone portion;
wherein interconnecting said collet with a graspable member alternatively includes selectively connecting said collet to said drill motor such that said drill motor is able to rotate said collet and driving said harvesting member includes rotating said harvesting member with said drill motor and pressing said harvesting member into the selected bone portion.

11. The method of claim 10, further comprising:
disposing said harvesting member with said trapped selected length of bone relative to an implant site; and
wherein removing said selected length of bone includes pushing said selected length of bone into the implant site.

12. The method of claim 10 further comprising:
disposing a plunger through at least a portion of said harvesting member;
wherein removing said selected length of bone includes pushing said selected length of bone from said harvesting member into the implant site with the plunger.

13. The method of claim 10, wherein interconnecting said harvesting member with said collet in a quick-release manner further includes positioning said harvesting member over a member having a member cannula and moving a collar within a throughbore of a sleeve against said biasing member to allow a pin to engage the harvesting member and remain exterior to at least said member cannula;
wherein said harvesting member includes a first end and a second end, wherein removing said selected length of bone includes removing the selected length of bone from at least one of the first end and the second end.

14. An instrument for harvesting a selected bone core, comprising:
a graspable member operable to be grasped by a user;
a harvest member operable with said graspable member to harvest the selected bone core; and
a connecting assembly including a connecting member having a connecting member cannula and a spring biasing member and a bearing member positioned within a sleeve, said connecting assembly operable to selectively interconnect said graspable member and said harvest member at least with said harvest member encompassing a portion of said connecting member;
wherein said graspable member includes an impact handle or a drill motor, wherein either of said impact handle or said drill motor are selectively engaged with said connecting member;
wherein said bearing member engages a bearing aperture of the harvest member in a quick release manner to selectively hold said harvest member relative to said graspable member and said bearing member remaining substantially external to said connecting member cannula;
wherein said spring biasing member compresses between said harvest member and a wall within said sleeve when said bearing member is engaged to said harvest member.

15. The instruments of claim 14, wherein said harvest member includes a cannula operable to be aligned with said connecting member cannula and a cutting end including at least one of a sharpened edge or a saw tooth.

16. The instrument of claim 14, wherein said connecting member couples with said harvest member;
wherein said harvest member can be coupled and uncoupled from said connecting member with a substantially axial motion alone.

17. The instrument of claim 14, wherein said harvest member is removably couplable to said a connecting member.

18. The instrument of claim 14, wherein said graspable member is removably couplable to said connecting member.

19. An instrument for forming a selected core of a bone, comprising:
a harvesting member operable to be driven into a selected portion of the bone, said harvesting member having a bearing aperture, wherein said harvesting member defines a harvesting cannula including a dimension substantially equal throughout a length of said harvesting member;
a graspable portion extending from said harvesting member such that said harvesting member can be positioned relative to the selected portion of bone for forming the bone core; and
a collet assembly including a sleeve defining an internal sleeve bore with a biasing spring member, a member having a member cannula, and a bearing member at least partially positioned within said internal sleeve bore;
wherein the biasing spring member is compressed by said member when said harvesting member is moved against said member to encompass at least a portion of the member and said bearing member engages said bearing aperture when said harvesting member and said graspable portion are interconnected;
wherein said bearing member extends through said bearing aperture and contacts a bearing locking depression in said sleeve to hold said member in a selected position and hold said harvesting member relative to said graspable portion while said bearing member is maintained substantially external to said member cannula.

20. The apparatus of claim 19, further comprising:

a plunger member;

wherein said plunger member is operable to be moved through said harvesting cannula and said member cannula simultaneously to remove the selected bone core from said harvesting cannula.

\* \* \* \* \*